United States Patent [19]
Burr et al.

[11] Patent Number: 5,037,755
[45] Date of Patent: Aug. 6, 1991

[54] MONOCLONAL ANTIBODY AND METHOD FOR DIAGNOSING GRAPE DISEASE EMPLOYING SAME

[75] Inventors: Thomas J. Burr; Andrew L. Bishop; Veronica L. Mittak, all of Geneva, N.Y.

[73] Assignee: Cornell Research Foundation, Inc., Ithaca, N.Y.

[21] Appl. No.: 127,310

[22] Filed: Dec. 2, 1987

[51] Int. Cl.$^5$ .................... C12N 5/20; C07K 15/28; C12P 21/08
[52] U.S. Cl. .............................. 435/210.27; 530/387; 935/104; 935/108; 935/110; 435/70.21; 435/172.2
[58] Field of Search ................ 530/387, 809; 435/240.27, 252.2; 935/104, 108, 110

[56] References Cited

PUBLICATIONS

Bazzi et al. Phytopath Medit. 27:51-56 1988.
Bazzi, C. et al. "Detection of *Agrobacterium Tumefaciens* in Grapevine Cuttings", *Bull OEPP* (Organ. Eur. Mediterr. Prot. Plant.) 17(1): 105-112, 1987, Cited in Dialog, Accession #0017541887, Brosis Number: 84018947.
Burr, T. J. et al., "Isolation of Agrobacterium Tumefaciens Biovar3 from Grapevine Galls and Sapand from Vineyard Soil", *Phytopathology* 73(20:163-165, 1983, Cited in Dialog, Accession #0013333181, Brosis Number: 76090673.
International Journal of Systematic Bacteriology, Jul. 1990, pp. 236-241, vol. 40, No. 3, Ophel and Kerr, for "Agrobacterium Vitis Sp. Nov. for Strains of Agrobacterium Biovar 3 from Grapevines".

*Primary Examiner*—Esther L. Kepplinger
*Assistant Examiner*—Paula Hutzell
*Attorney, Agent, or Firm*—Sughrue, Mion, Zinn, Macpeak & Seas

[57] ABSTRACT

A monoclonal antibody specific to *Agrobacterium tumefaciens* biovar 3. A method of diagnosing *Agrobacterium tumefaciens* biovar 3 associated grapevine disease comprising: (1) culturing bacteria from grapevine tissue suspected of being infected with *Agrobacterium tumefaciens* biovar 3; (2) reacting the bacteria with a monoclonal antibody specific to *Agrobacterium tumefaciens* biovar 3 under conditions sufficient to form an antigen-antibody complex between antigens specific to *Agrobacterium tumefaciens* biovar 3 and the monoclonal antibody; and (3) detecting the presence of the antigen-antibody complex. A method for diagnosing *Agrobacterium tumefaciens* biovar 3 associated grapevine disease from crown gall tissue comprising: (1) preparing separate suspensions of ground gall tissue to be diagnosed and of ground wood of the same cultivar as a control; (2) separately reacting specific to *Agrobacterium tumefaciens* biovar 3 under conditions sufficient to form an antigen-antibody complex between antigens specific to *Agrobacterium tumefaciens* biovar 3 and the monoclonal antibody; (3) assaying for the presence of the antigen-antibody complex ; and (4) comparing the assay results for the gall tissue to be diagnosed to the assays results for the wood control. A method for diagnosing *agrobacterium tumefaciens* biovar 3 associated grapevine disease from nonsymptomatic grapevine cuttings comprising: (1) separately flushing fluid through cuttings to be diagnosed and through uninfected control cuttings; (2) separately reactign the fluid flushed through the cuttings with monoclonal antiody specific to *agrobacterium tumefaciens* biovar 3 under conditions sufficient to form an antigen-antibody complex between antigens specific to *Agrobacterium tumefaiens* biovar 3 and the monoclonal antibody; (3) assaying for the presence of the antigen-antibody complex; and (4) comparing the assay results for said cuttings to be diagnosed to the assay results for the control cuttings. A hybridoma that secretes the above-described monoclonal antibody and a method of producing the hybridoma.

2 Claims, No Drawings

MONOCLONAL ANTIBODY AND METHOD FOR DIAGNOSING GRAPE DISEASE EMPLOYING SAME

FIELD OF THE INVENTION

The present invention relates to a novel monoclonal antibody and a method for diagnosing grape disease employing the monoclonal antibody. More specifically, the present invention relates to a monoclonal antibody specific to tumorigenic and nontumorigenic *Agrobacterium tumefaciens* biovar 3 and a method for detecting grapevine disease, such as grapevine crown gall, regardless of tumorigenicity.

The present invention also relates to a novel hybridoma that secretes the monoclonal antibody and to a method of producing the hybridoma.

BACKGROUND OF THE INVENTION

*Agrobacterium tumefaciens* biovar 3, the causal agent of crown gall of grapevine (Vitis spp.) (Burr, T.J., and Katz, B.H. 1984. Grapevine cuttings as potential sites of survival and means of dissemination of *Agrobacterium tumefaciens*. Plant Dis. 68:976-978; Kerr, A. and Panagopoulos, C.G. 1977. Biotypes of *Agrobacterium radiobacter* var. *tumefaciens* and their biological control. Phytopathol. Z. 90:172-179; Panagopoulos, C.G., and Psallidas. P.G. 1973. Characteristics of Greek isolates of *Agrobacterium tumefaciens* (E.F. Smith & Townsend) Conn. J. Appl. Bacteriol. 36:233-240; and Sule, S., 1978. Biotypes of *Agrobacterium tumefaciens* in Hungary. J. Appl. Bacteriol. 44:207-213) survives benignly in grapevine xylem, and is transmitted by vegetative propagation (Burr. T.J., and Katz. B.H. 1984. Grapevine cuttings as potential sites of survival and means of dissemination of *Agrobacterium tumefaciens*. Plant Dis. 68:976-978 and Lehoczky. J. 1968. Spread of *Agrobacterium tumefaciens* in the vessels of the grapevine after natural infection. Phytopathol. Z. 63:239-246). Tumor production follows wounding of systemically infested vines by winter injury or mechanical means (Dhanvantari, B.N. 1983. Etiology of grape crown gall in Ontario. Can. J. Bot. 61:2641-2646; Lehoczky. J. 1968. Spread of *Agrobacterium tumefaciens* in the vessels of the grapevine after natural infection. Phytopathol. Z. 63:239-246; and Lehoczky. J. 1978. Root system of the grapevine as a reservoir of *Agrobacterium tumefaciens* cells. Proc. 4th Int. Conf. Plant Path. Bact. (Angers, France) 1:239-243). Possible strategies for controlling spread of the pathogen include indexing and certification of propagation wood (Tarbah. F.A., and Goodman. R.N. 1986. Rapid detection of *Agrobacterium tumefaciens* in grapevine propagating material and the basis for an efficient indexing system. Plant Dis. 70:566-568). Several methods for testing propagation stocks have been proposed, one relies on colony appearance on selective media (Tarbah, F.A., and Goodman, R.N. 1986. Rapid detection of *Agrobacterium tumefaciens* in grapevine propagating material and the basis for an efficient indexing system. Plant Dis. 70:566-568). However, endophytic bacteria similar in appearance to *Agrobacterium tumefaciens* biovar 3 on selective medium are present in grape xylem and this can lead to unnecessary rejection of plant material in an indexing scheme depending exclusively on colony appearance for diagnosis. Subsequent testing of numerous strains to identify *Agrobacterium tumefaciens* biovar 3 is time consuming. and labor intensive (Miller, H.J., and Vruggink, H. 1981. An assessment of biochemical and serological tests for *Agrobacterium radiobacter* subsp. *tumefaciens*. Phytopath. Z. 102:292-300 and Moore, L.W., Anderson, A., and Kado, C.I. 1980. *Agrobacterium*. In Laboratory Guide for Identification of Plant Pathogenic Bacteria, N.W. Schaad, ed., pp. 17-25. American Phytopathological Society, St. Paul). Serological assays provide more reliable diagnosis, but the presence of common epitopes in nontarget bacterial species can lead to false positive diagnoses due to cross reacting sera (Calzolari, C., Bazzi, C., and Mazzuchi, U. 1982. Cross-reactions between *Corynebacterium sepedonicum* and *Arthrobacter polychromogenes* in immunofluorescent staining. Potato Res. 25:239-246 and Crowley, C.F., and DeBoer, S.H. 1982. Nonpathogenic bacteria associated with potato stems cross-react with *Corynebacterium sepedonicum* in immunofluorescence. Am. Potato J. 59:1-7). Also, previous attempts to develop biovar-specific antisera have not been successful (Keane, P.J., Kerr, A., and New, P.B. 1970. Crown gall of stone fruit. II. Identification and nomenclature of *Agrobacterium* isolates. Aust. J. Biol. Sci. 23:585-595 and Miller, H.J., and Vruggink, H. 1981. An assessment of biochemical and serological tests for *Agrobacterium radiobacter* subsp. *tumefaciens*. Phytopath. Z. 102:292-300).

Hybridoma techniques, developed by Köhler and Milstein (Köhler, G., and Milstein, C. 1975. Continuous cultures of fused cells secreting antibodies of predefined specificity. Nature 256:495-497), allow production of antibodies specific to single epitopes, selected according to the investigators' design, thereby eliminating the problem of cross-reaction. Application of monoclonal antibodies to diagnosis or detection of several bacterial plant pathogens has been reported (Alvarez, A.M., Benedict, A.A., and Mizumoto, C.Y. 1985. Identification of *Xanthomonas compestris* pv. *campestris* with monoclonal antibodies. Phytopathology 75:722-728: De Boer and Wieczorek, A. 1984. Production of monoclonal antibodies to *Corynebacterium sepedonicum*. Phytopathology 74:1431-1434 and Halk, E.L., and De Boer, S.H. 1985. Monoclonal antibodies in plant disease research. Ann. Rev. Phytopathol. 23:321-350).

The production of a monoclonal antibody specific to *Agrobacterium tumefaciens* biovar 3 for application to detection and diagnosis of grape crown gall would be of great importance to the grape industry.

SUMMARY OF THE INVENTION

Accordingly, one object of the present invention is to provide a reliable serological reagent for identification of *Agrobacterium tumefaciens* biovar 3.

A second object of the present invention is to provide a serological reagent for identification of *Agrobacterium tumefaciens* biovar 3 that is independent of strain variation.

A further object of the present invention is to provide a serological reagent for rapid diagnosis of *Agrobacterium tumefaciens* biovar 3 in culture.

An even further object of the present invention is to provide a diagnostic method for identification of *Agrobacterium tumefaciens* biovar 3 in culture that is simpler to perform and interpret than previously known methods for diagnosis of *Agrobacterium tumefaciens* biovar 3.

Still another object of the present invention is to provide a diagnostic method for direct diagnosis of *Agrobacterium tumefaciens* biovar 3 in infected grapevine tissue.

These and other objects have been attained by providing a monoclonal antibody specific to *Agrobacterium tumefaciens* biovar 3, methods for direct diagnosis of *Agrobacterium tumefaciens* biovar 3 in infected grapevines and a method for diagnosis of *Agrobacterium tumefaciens* biovar 3 in culture.

One method for direct diagnosis is a method for diagnosing *Agrobacterium tumefaciens* biovar 3 associated grapevine disease from crown gall tissue comprising: (1) preparing separate suspensions of ground gall tissue to be diagnosed and of ground wood of the same cultivar as a control: (2) separately reacting said ground suspensions with a monoclonal antibody specific to *Agrobacterium tumefaciens* biovar 3 under conditions sufficient to form an antigen-antibody complex between antigens specific to *Agrobacterium tumefaciens* biovar 3 and the monoclonal antibody; (3) assaying for the presence of the antigen-antibody complex; and (4) comparing the assay results for the gall tissue to be diagnosed to the assay results for the wood control.

Another method for direct diagnosis is a method for diagnosing *Agrobacterium tumefaciens* biovar 3 associated grapevine disease from nonsymptomatic grapevine cuttings comprising: (1) separately flushing fluid through cuttings to be diagnosed and through uninfected control cuttings; (2) separately reacting said fluid flushed through said cuttings with a monoclonal antibody specific to *Agrobacterium tumefaciens* biovar 3 under conditions sufficient to form an antigen-antibody complex between antigens specific to *Agrobacterium tumefaciens* biovar 3 and said monoclonal antibody; (3) assaying for the presence of the antigen-antibody complex; and (4) comparing the assay results for said cuttings to be diagnosed to the assay results for said control cuttings.

The method for diagnosis of *Agrobacterium tumefaciens* biovar 3 in culture comprises: (1) culturing bacteria from grapevine tissue suspected of being infected with *Agrobacterium tumefaciens* biovar 3; (2) reacting the bacteria with a monoclonal antibody specific to *Agrobacterium tumefaciens* biovar 3 under conditions sufficient to form an antigen-antibody complex between antigens specific to *Agrobacterium tumefaciens* biovar 3 and said monoclonal antibody; and (3) detecting the presence of said antigen-antibody complex.

The present invention also provides a hybridoma that secrets the above-described monoclonal antibody and a method of producing the hybridoma.

DETAILED DESCRIPTION OF THE INVENTION

For the purpose of this invention, the nomenclature "Agrobacterium tumefaciens biovar 3" means the group of all biovar 3 strains of the bacterial species *Agrobacterium tumefaciens*, which species includes the tumorigenic and nontumorigenic subspecies, namely subspecies *tumefaciens* (tumorigenic) and subspecies *radiobacter* (nontumorigenic).

The monoclonal antibody according to the present invention is specific to *Agrobacterium tumefaciens* biovar 3.

In a preferred embodiment, the monoclonal antibody is one having the identifying characteristics of monoclonal antibody AbF21-1D3G7C8 which is produced by the murine hybridoma line F21-1D3G7C8. The murine hybridoma line F21-103G7C8 was deposited July 1, 1987 with the American Type Culture Collection, 12301 Parklawn Drive, Rockville, MD 20852. The culture was given accession number HB 9463.

Monoclonal antibody AbF21-1D3G7C8 is of the IgG1 isotype.

The monoclonal antibody according to the present invention can be obtained from hybridomas produced according to the techniques developed by Köhler and Milstein (Köhler, G., and Milstein, C. 1975. Continuous cultures of fused cells secreting antibodies of predefined specificity. Nature 256:495–497). Thus a third aspect of the present invention provides a hybridoma that secretes a monoclonal antibody specific to *Agrobacterium tumefaciens* biovar 3, and a fourth aspect of the present invention provides a method for producing the hybridoma.

In order to produce the hybridoma of the present invention, suitable hosts, such as mice or rats, preferably BALB/c mice, are immunized with immunogen in a suitable adjuvant. Preferably, immunization is both intraperitoneally and subcutaneously. Booster injections are administered at suitable times, readily determined by the skilled artisan after the initial immunization.

The immunogen used in the present invention for production of antibodies can be any biovar 3 strain of the bacteria *Agrobacterium tumefaciens*.

The *Agrobacterium tumefaciens* biovar 3, Strain CG-49 was deposited Oct. 16, 1987 with the American Type Culture Collection, 12301 Parklawn Drive, Rockville, MD 20852. The culture was given accession number 53691.

The immunogen can be prepared by conventional methods.

For example, bacterial cultures, grown according to conventional methods, such as on potato dextrose agar (PDA) at 28° C., are harvested by washing the plates with a suitable buffer, such as calcium-magnesium-free phosphate buffered saline (PBS-CMF: 1.5 mM $KH_2PO_4$, 8.1 mM $Na_2PO_4$, 2.7 mM KCl, 150 mM NaCl, pH 7.4). The bacteria are then washed to remove some extracellular polysaccharide. A suitable procedure is to wash by three cycles of centrifugation (10.000 $\times$g, 10 min) and resuspension in PBS-CMF. The washed bacterial suspensions are then adjusted to an appropriate concentration for immunization with a suitable buffer, e.g. PBS-CMF. Appropriate concentrations are readily determined by the skilled artisan, and for example range from about $5 \times 10^7$ to about $5 \times 10^8$ colony forming units (cfu) per ml.

The suspensions are heated prior to immunization in order to inactivate flagellar antigens. Suitable heating conditions are heating for 10 minutes at 80° C.

The thus prepared immunogen is mixed with a suitable adjuvant in a ratio of about 1:1 for immunizations. A suitable adjuvant for the initial immunization is Freund's complete adjuvant. For booster injections, a suitable adjuvant is Freund's incomplete adjuvant.

After a period of time sufficient for antibodies to be detectable in whole serum, the spleens of the immunized hosts are removed by conventional techniques and splenocytes are fused with myeloma cells.

A suitable method which can be used for detecting the presence of antibodies in whole serum is the microELISA procedure described below. Specifically, a sample of mouse (or other host) whole serum is collected and subjected to the microELISA procedure. If antibodies are detected, the spleens can be removed and the splenocytes fused.

Fusion is by known methods, for example by the polyethylene glycol technique. The standard fusion methods and techniques for performing the splenectomy are described in, for example. "Monoclonal Hybridoma Antibodies: Techniques and Applications. Hurrell, John G.R. Editor, CRC Press", Inc. Boca Raton. FL (1982), 231 pp. and "Monoclonal Antibodies: Principles and Practice. Second Edition. Goding. James W. Academic Press", (1986) 293 pp.

As the myeloma cells, there can be used any myeloma cell lines that are sensitive to the selective medium, do not produce antibodies themselves and can grow indefinitively in culture.

Examples of publicly available myeloma cell lines that can be used according to the present invention include SP2/O-AG14 (a murine myeloma cell line available from the American Type Culture Collection); P3-x63-Ag8 (Köhler, G. and Milstein, C. *Nature* (London) 256:495 (1975)): P3-NS1/1-Ag4-1 (Köhler, G. et al., *Eur. J. Immunol.* 6:292 (1976)): P3-x63-Ag8.653 (Köhler, G. et al. *Eur. J. Immunol.* 6:292 (1976)); SP2/O-Ag14 (Shulman, M et al. *Nature* (London) 276:269 (1978)): FO (Fazekas de St. Groth, S. and Scheidegger, D. *J. Immunol. Methods* 35:1 (1980)) and 210-RCY3-Ag1 (Galfre, G. et al., *Nature* 277:131 (1979)).

A preferred myeloma cell line for use in the present invention is SP2/O-AG14.

The fused cells are cultured in an appropriate selective medium, readily determined by the skilled artisan.

According to the present invention, if SP2/O-AG14 myeloma cells are used, an appropriate selective medium is DMEM/HAT/20%FBS (Dulbecco's Modified Eagle Medium. 0.45% glucose supplemented with 1.5 mM HEPES, 44 mM NaHCO$_3$, 0.1 mM nonessential amino acids, 2 mM L-glutamine, 0.45 mM sodium pyruvate, $10^5$ units/liter penicillin G, $10^5$ units/liter streptomycin, 20% fetal bovine serum (FBS), and $1.02 \times 10^{-4}$ M hypoxanthine, $4 \times 10^{-7}$ M aminopterin, $1.65 \times 10^{-4}$ mM thymidine (HAT)).

Desirably, culture plates are seeded with feeder cells by conventional techniques ("Monoclonal Hybridoma Antibodies" Techniques and Applications. Hurrell, John G.R. Editor, CRC Press, Inc., Boca Raton, FL (1982), 231 pp.).

According to the present invention, if mice are used as the host, culture plates are seeded one day prior to use with mouse macrophages collected by peritoneal lavage of pristane-primed mice.

The fused cells are cultured until distinct colony growth can be observed in the wells with a microscope. At that time, cells are fed with culture media using standard procedures. As cultures become old the medium turns from a red color to a yellow color indicating a pH change. After about two feedings, the supernatant in the cell cultures is tested for the presence of antibody. This occurs after a period of about 4 to 6 days.

One skilled in the art can readily determine suitable culture conditions.

After an appropriate culture period, hybrids secreting antibodies that react with *Agrobacterium tumefaciens* biovar 3 are cloned and subcloned by limiting dilution, i.e., by diluting to a point where less than one cell per new culture will be expected and then plating into the wells ("Monoclonal Hybridoma Antibodies" Techniques and Applications. Hurrell, John G.R. Editor, CRC Press, Inc., Boca Raton, FL (1982), 231 pp.).

In order to screen the hybridomas that secrete antibodies that react with *Agrobacterium tumefaciens* biovar 3, a microELISA, can be used as follows.

Antigens are prepared by making suspensions of heat killed strains to be tested in coating buffer (40 mM sodium carbonate, 0.05% NaN$_3$, pH 9.6) and adjusting to OD$_{600nm}$=0.1 ($\sim 10^8$ cfu/ml). The bacteria should be from 3 to 5 day old cultures grown in 523 or RS media (523 medium: per liter, 10 g sucrose, 8 g casein hydrolysate, 4 g yeast extract, 3 g K$_2$HPO$_4$, 0.2 g MgSO$_4$·7H$_2$O, 15 g agar, pH 7.0 (Kado. E.J. et al., Physiol. Plant Pathol. 2:47-57 (1972). RS medium: 0.20 g/L MgSO$_4$; 0.90 g/L K$_2$HPO$_4$; 0.70 g/L KH$_2$PO$_4$; 4.0 g/L adonitol; 0.14 g/L yeast extract; 0.20 g/L NaCl; 1.0 g/L boric acid; and 15.0 g/L agar; pH 7.2. The mixture is autoclaved and cooled to 50° C. and the following are added by filter sterilization: 0.08 g/L triphenyl tetrazolium chloride; 0.02 g/L D-cycloserine, 0.02 g/L trimethoprim; and 0.25 g/L cycloheximide.). The bacteria can be heat killed by heating for 10 minutes at 80° C.

The suspensions are then distributed in wells of microtitre plates (about 100 μl/well) and incubated overnight in moist chambers at 37° C.

After incubation, moisture is flicked out and the wells are washed with a suitable buffer (e.g., PBS+0.05% Tween 20—PBST) and then blocking buffer (50 mM TrisHCl, 5% non-fat dry milk, 0.05% NaN$_3$ pH 7.2) is added (about 200 μl/well) to block nonspecific binding sites. The plates are incubated with the blocking buffer for 1 hour at room temperature in a moist chamber. The wells are then washed as above with a suitable buffer (e.g. PBST).

Hybridoma culture supernatant (about 100 μl/well) is added and the plates are incubated in a moist chamber at 37° C. in 5% CO$_2$ (to maintain the pH) for about 2.5 hours. Wells are again washed as above.

Nonspecific binding sites are next blocked by adding blocking buffer (about 200 μl/well) which has been heated to 55° C. and incubating in a moist chamber for about 20 minutes at room temperature. Wells are again washed as above.

Labelled anti-host antibody complexes are then prepared by adding a suitable amount of anti-host antibody having a suitable label. In the present system, using mice as hosts, alkaline phosphatase conjugated anti-mouse IgG in PBST is preferably used. The alkaline phosphatase conjugated anti-mouse IgG is diluted according to a tested optimum concentration which can readily be determined by the skilled artisan, added to the wells (about 100 μl/well), and the plates are incubated at 37° C. in a moist chamber for a time sufficient to saturate specific binding sites (e.g. about 1.5 hours).

The wells are again washed and the amount of binding determined by means appropriate for the label used. For an alkaline phosphatase label, a p-nitrophenyl phosphate substrate is added and incubated for a period of time sufficient to observe a reaction.

The p-nitrophenyl phosphate is suitably used at a concentration of 1 mg/ml in 9.7% diethanolamine, pH 9.8, and about 200 μl are added per well. The results can be assessed by visual observation or spectrophotometrically at 405 nm.

Monoclonal antibodies according to the present invention can be produced in quantity by growing large batches of hybridoma cell cultures and purifying the antibody from the supernatant or by injecting mice with the hybridoma line to stimulate the production of acites fluid. Both methods are well known in the art and are described in, for example, "Monoclonal Hybridoma Antibodies" Techniques and Applications. Hurrell, John G.R. Editor, CRC Press. Inc., Boca Raton, FL (1982) 231 pp.

The hybridomas of the present invention can be grown in large batches by inoculating 20 ml lots of a suitable medium, such as DMEM/20% FBS media, with hydriboma and culturing 7-10 days at 37° C. in the presence of 5% $CO_2$ (DMEM/20% FBS: Dulbecco's Modified Eagle Medium, 0.45% glucose supplemented with 1.5 mM HEPES, 44 mM $NaHCO_3$, 0.1 mM nonessential amino acids, 2 mM L-glutamine, 0.45 mM sodium pyruvate, $10^5$ units/liter penicillin G, $10^5$ units/liter streptomycin. 20% fetal bovine serum (FBS)).

The monoclonal antibody can be purified by known methods, for example, by affinity separation using protein A. (Miller, T.J., Stone, H.O. 1978. The rapid isolation of ribonuclease free immunoglobulin G by protein A-sepharose affinity chromatography, J. Immunol. Methods 24:111-125).

According to the present invention, affinity separation using protein A is preferred, and an especially preferred modification of this method uses the AFFI-GEL, PROTEIN A MAPS II KIT commercially available from Bio-Rad Laboratories, Richmond, CA. In this method, using the Bio-Rad Laboratories' kit, 50 ml of culture supernatant is mixed with 50 ml Bio-Rad binding buffer and applied to a 5 ml bed volume of Affi-gel protein A in a 1×10 cm column. The column is washed with 50 ml of Bio-Rad binding buffer and IgG is eluted with 20 ml of Bio-Rad elution buffer or until the absorbance of the eluate at 280 nm approaches 0. The fractions of IgG are combined and neutralized with 32 $\mu$l/ml 1 M Tris HCl, pH 9.0. The protein concentration can be estimated by measuring the absorbance by known methods.

The specificity of the monoclonal antibody according to the present invention can be determined by testing binding to various strains of Agrobacterium biovar 3, Agrobacterium biovar 2, Agrobacterium biovar 1, various strains from other genera and various strains of unidentified saprophytes associated with grapevines in the field. The monoclonal antibody according to the present invention reacts with strains of Agrobacterium biovar 3 but does not react with any of the other above-mentioned bacteria. Also, the specificity of the monoclonal antibody according to the present invention is not affected by tumorigenicity of Agrobacterium biovar 3.

The specificity of the monoclonal antibody according to the present invention can be tested by using a modification of the above-described microELISA technique. Specifically, the microELISA is modified for testing of large numbers of strains by drying antigens suspended in coating buffer in a 37° C. circulating air incubator, rather than by coating overnight in a moist chamber. Then, immediately prior to use, the dried plates are incubated with fixative (25% ethanol, 10% acetic acid) for about 15 minutes at room temperature and then rinsed with distilled water. The present inventors have found that drying and fixation of the antigens on plates significantly improves the microELISA tests. The microELISA protocol described previously can then be followed except that incubation with the monoclonal antibody is performed in a moist chamber at 37° C. in air, not in 5% $CO_2$, and purified monoclonal antibody, rather than hybridoma culture supernatant, is used.

An important embodiment of the present invention is the provision of methods of diagnosing grape disease. The methods are all based on immunoassays and are useful for detecting the pathogen Agrobacterium tumefaciens biovar 3 in many types of plant tissues including gall tissue and tissue from symptomless, systemically infected plants.

More specifically, the methods of diagnosis involve conducting immunoassays on cultures of plant pathogens, i.e., plant pathogens that have been cultured on selective medium for the presence of Agrobacterium tumefaciens biovar 3 or conducting immunoassays directly on plant pathogens in plant material. Further, the methods can be conducted on numerous types of infected plant tissue, including, for example, crown gall tissue and symptomless, systemically infected grape cuttings.

As the immunoassay, any immunoassay can be used as long as the method of detecting the results of the assay is capable of generating a readable signal.

Examples of immunoassays suitable for use in the diagnostic methods according to the present invention include microELISA's (Yuen, G.Y., Alvarez, A.M., Benedict A.A., and Trotter, K.J., 1987. Use of monoclonal antibodies to monitor the dissemination of Xanthomonas campestris pv. campestris. Phytopathology 77:366-370 and Lin, C.P., Chen, T.A., Wells J.M., van der Zvet, T. 1987. Identification and detection of Erwinia amylovora with monoclonal antibodies. Phytopathology 77:376-380), immunoblots or dot-immunobinding (Leach, J.E., Ramundo, B.A., Pearson, D.L. and Claflin, L.E. Dot-immunobinding assay for detecting Xanthomonas campestris pv. holcicola in sorghum. Plant Disease 71:30-33), and immunofluorescence. (Slack S.A., Kelman A. and Perry, J.W. 1979. Comparison of three serodiagnostic assays for detection of Corynebacterium sepedonicum. Phytopathology 69:186-189).

One preferred immunoassay for use in the diagnostic methods according to the present invention is an immunoblot or dot-immunobinding assay as described, for example, in Leach, J.E., Ramundo, B.A., Pearson, D.L. and Claflin, L.E. Dot-immunobinding assay for detecting Xanthomonas campestris pv. holcicola in sorghum. Plant Disease 71:30-33.

An especially preferred immunoassay for use in the diagnostic methods according to the present invention is the modified microELISA described above. wherein both of the steps of drying and fixation of the antigens on plates are performed.

On the other hand, one immunoassay that is not preferred for use in the diagnostic methods according to the present invention is an indirect fluorescent antibody stain (IFAS) assay. (Slack S.A., Kelman A. and Perry, J.W. 1979. Comparison of three serodiagnostic assays for detection of corynebacterium sepedonicum. Phytopathology 69:186-189). This is because the signal is too weak to make a definitive diagnoses by visualization with the human eye as to the presence or absence of Agrobacterium tumefaciens biovar 3, even at high concentrations of monoclonal antibody (e.g., 40 $\mu$g/ml) and fluorescein isothiocyanate anti-antibody conjugate. However, with suitable amplification means, e.g. computer visualization, a more preferred embodiment would be achieved.

In all diagnostic assays, suitable controls are conducted in parallel. These controls can be readily determined by the skilled artisan.

Cultures of plant pathogens for use with the various immunoassays in the diagnostic methods using plant pathogens that have been cultured from plant tissue can be made by several methods.

One method is a modification of the method described by Legiczky (Vitis 10:215–221 (1971)) and Burr and Katz (Plant Disease 68, No. 11:976–978 (1984). Cuttings of suitable size (e.g. 10–25 cm (3 nodes)) are taken with pruning shears and surface-sterilized in an appropriate solution, such as 0.53% NaOCl, for a time sufficient to eliminate epiphytic microflora. When 0.53% NaOCl is used, a suitable sterilization time is about 3 minutes. A portion (about 1 cm) is then cut from each end of the cutting to remove any residual sterilization solution. The sterilized cuttings can be rooted, if desired, in a sterile potting medium such as sand, Cornell mix (a peat based potting medium) (Boodley J.W. and Sheldrake, R., Cornell Inf. Bull. 43:1–8 (1970)), or vermiculite, under conditions of 100% humidity and 22°–25° C. until callus is initiated at the base of the cuttings.

Tissue pieces can be isolated from the callus with a sterile scalpel and macerated in sterile water with suitable equipment such as a mortar and pestle. The size of the tissue pieces should be about 0.1–0.3 g. The amount of distilled water used per tissue piece for maceration is about 1 ml/g tissue. If desired, the surfaces of the tissue pieces can be quickly sterilized with ethyl alcohol and washed with sterile water before macerating in order to eliminate superficial microflora.

After maceration, the tissue pieces can be separated from the liquid, the liquid diluted if necessary, and then smeared onto the surface of suitable selective medium for biovar 3. Alternatively, the macerated mix can be smeared directly onto the medium.

Suitable selective media include RS medium described above.

The cultures are incubated 4 to 5 days at 28° C. in a thermostat for colony formation.

A second method of culturing *Agrobacterium tumefaciens* biovar 3 from cuttings involve flushing water though cuttings with vacuum pressure, as described by Bazzi et al (*Bulletin OEPP/EPPO Bulletin* 17:105–112 (1987)).

In this method cuttings (about 10 to 20 cm long, 6 to 12 mm in diameter, with 1 to 3 nodes ) are pruned from dormant vines or taken from storage, washed under running tap water and blotted dry. The proximal end of each cutting is fitted with a piece of tubin that leads to a collection vessel, e.g. a test tube inside a vacuum flask, that can be placed under vacuum. The distal end of the cutting is fitted with tubing leading from a vessel containing a "washing fluid". A suitable washing fluid is sterile distilled water. Washing fluid is then forced through the cutting into the collection vessle by reducing pressure in the vacuum flask.

Cultures are prepared by smearing aliquots of the washing fluid from the collection vessel onto suitable selective media as described above and incubated as described above.

When the diagnostic method used with the cultured microorganisms is the above-described microELISA or modified microELISA, controls can also be run as follows:

(1) a positive control comprising a cultured known biovar 3, such as CG49;

(2) a negative control comprising a cultured known biovar 1 (e.g. strain C58) and a cultured known biovar 2 (e.g. strain K84); and (3) an additional negative control comprising no microorganisms.

With this system of controls, when the reaction with monoclonal antibody is evaluated, the speciman is considered positive, i.e. infected with *Agrobacterium tumefaciens* biovar 3 if: (1) one or more colonies from a given cutting gives a reaction significantly stronger than the negative control comprising known biovar 1 and biovar 2 strains, and (2) the reactions with the biovar 1 and biovar 2 negative control samples are not significantly different from the reaction of the negative control comprising no microorganisms.

The determination of whether a reaction is signficantly stronger or not can be made by visual inspection or by comparison of spectrophotometer readings of the reacted samples using a Students' T-test as described in, for example, *Statistical Methods,* 6th edition. George W. Snedeco and Wm. G. Cochran, Iowa State University Press, Ames, Iowa, 693 pp.

Further, using the above system of controls, if the reaction of the biovar 1 and biovar 2 negative controls is stronger than the reaction of the negative control comprising no microorganisms, or if the reaction of the biovar 3 positive control is not significantly stronger than the reaction of the biovar 1 and 2 negative controls, the diagnostic test is invalid and must be repeated.

When the diagnostic method used with the cultured microorganism is the above-described immunoblot procedure, the following controls can preferably be run: (1) a positive control comprising a cultured known biovar 3, and (2) a negative control comprising a cultured known biovar 1 and a cultured known biovar 2. Further in addition to preforming the immunoblot procedure on one or more membranes (membrane A), a control immunoblot procedure can be carried out on one or more membranes (membrane B) wherein buffer (e.g. unamended PBST) is substituted for the monoclonal antibody. Membranes B serve as a control for non-specific binding of the second antibody to microorganisms.

In this procedure, using the above system of controls, the specimen is considered positive when one or more clones from a given cutting on membranes A give a reaction signficantly stronger than: (1) the reaction of the negative controls biovar 1 and 2 on membrane A, and (2) the reaction of the specimen colonies on membranes B. The reaction strength is determined by visual inspection of spots in color and density. One skilled in the art can readily determine significant differences by visual inspection.

Further, if the reaction of the biovar 1 and 2 negative controls on membrane A is signficiantly stronger than on membrane B, or if the reaction of the biovar 3 positive control is not stronger on membrane A than on membrane B, or if the reaction of the biovar 3 position control is not stronger on membrane A than the reaction of the biovar 1 and 2 negative controls on membrane A, the diagnostic test is invalid and must be repeated.

When the diagnostic methods use immunoassays performed on plant pathogens directly from plant tissue without the intermediate step of culturing the pathogens, the pathogen preparations are prepared in one of two ways, depending upon whether crown gall tissue is to be diagnosed or whether nonsymptomatic grape cuttings are to be diagnosed.

For diagnosis from crown gall tissue, a suitably sized sample of gall tissue, for example, 0.2 to 1.0 gm, is triturated or macerated in a mortar and pestle in a liquid that will not interfere with subsequent assay steps, for example in distilled water, in an amount of about 5 ml per g tissue. A portion of wood from an uninfected plant of the same cultivar is treated in a similar manner to serve as a control.

Each preparation is then serially diluted in a suitable buffer, such as the above-described coating buffer, for coating a support, such as a well of a microtiter plate, with antigen by drying in a circulating air incubator as described above. Suitably sized samples, e.g. 100 μl, of each dilution are then transferred to a support, e.g., a well of microtiter ELISA plate, and dried in a circulating air incubator, e.g. overnight at 37°, or by incubating overnight in a moist chamber at 37° C. Each sample should desirably be present in a minimum of three replicate wells in order to be able to properly interpret the results.

A microtiter ELISA is then performed as described above and the results of the samples from the tissue to be diagnosed are compared to the results for the control samples. A significant difference is determined by Student's T-test (*Statistical Methods,* 6th edition. George W. Snederson and Wm. G. Cochran, Iowa State University Press, Ames, Iowa, 593 pp.) between the mean ELISA readings from the gall tissue samples and the control preparations at the same dilution indicate that the sample is positive, i.e. infected with *Agrobacterium tumefaciens* biovar 3.

An alternative method for detecting the presence of pathogen in gall tissue is to serially dilute ground samples prepared as described above in distilled water, apply aliquots from each dilution to nitrocellulose membranes, and perform an ELISA referred to above for nitrocellulose as a solid support. A parlllel control ELISA for nitrocellulose as a support wherein buffer (e.g. unamended PBST) is substituted for monoclonal antibody can also be run as described above. Where spots from gall samples are significantly stronger in color and density, as determined by visual inspection, from: (1) control preparations at the same dilution on membranes A, and (2) the gall samples on membranes B, the sample is positive. One skilled in the art can readily determine a significant difference by visual inspection.

If the parallel control ELISA using no monoclonal antibody is also run, the sample is considered positive if gall samples on the membrane wherein monoclonal antibody was used are also significantly stronger than the gall samples on the membrane wherein monoclonal antibody was not used.

Further, when the control membrane is run if uninfected wood controls react more strongly on membranes treated with monoclonal antibody than on membranes not treated with monoclonal antibody, the diagnostic test is invalid and must be repeated.

The second method for direct diagnosis is for diagnosing nonsymptomatic grapevine cuttings. In this method, cuttings are flushed, as described above, except that the flushing fluid is a buffer, such as the above-described coating buffer, which can be used for coating a support, such as a well of a microtiter plate, with antigen by drying in a circulating air incubator as described above. Cuttings known to be uninfected are used as negative controls.

The preparations are then diluted, generally tenfold, in the same flushing fluid and suitably sized samples, e.g. 100 μl of each dilution are transferred to a suppport, e.g. a well of microtiter ELISA plates, and dried in a circulating air incubator, e.g. overnight, or by incubating overnight in a moist chamber at 37° C.

A microtiter ELISA is performed and the results evaluated as described above for the direct diagnosis method using crown gall tissue.

Further, as for the direct diagnosis method using crown gall tissue, the direct diagnosis method using cuttings from nonsymptomatic plants can employ nitrocellulose membranes as an alternative method for detecting the presence of pathogen. When this method is used, the cuttings are flushed with distilled water, diluted in distilled water, and aliquots from the diluted preparations are applied to nitrocellulose membranes.

An ELISA for nitrocellulose as a solid support is performed and the results evaluated as described above for the direct diagnosis method using crown gall tissue.

The preferred immunoassays will now be described in terms of the best mode known to the inventors.

Enzyme-Linked Immunosorbent Assay (ELISA) with Agrobacterium

Stock solutions 0.5 M $Na_2HPO_4$ (dibasic)

35.5 g $Na_2HPO_4$ dilute to 500 ml.

0.5 M $NaH_2PO_4$ (monobasic)

30.0 g $NaH_2PO_4$ dilute to 500 ml.

0.5 M $NaPO_4$, pH 7.2

50 ml monobasic stock, 250 ml dibasic stock, adjust pH by adding more dibasic to raise pH. monobasic to lower pH.

5×PBST (50 mM $NaPO_4$, 4.5% NaCl, 0.5% Tween)

100 ml 0.5 M $NaPO_4$, pH 7.2 stock
45 g NaCl
5 ml Tween 20 (Sigma)
Make to 1 liter.

Solutions

PBST

Dilute 5×stock. Add 0.5 g/L $NaN_3$.

Coating buffer (40 mM $NaCo_3$, 0.05% $NaN_3$, pH 9.6)

1.59 g $Na_2CO_3$
2.93 g $NaHCO_3$
0.5 g $NaN_3$.
Make to 900 ml, adjust pH to 9.6, and bring to 1 liter.

Fixative (10% acetic acid, 25% ethanol)

100 ml glacial acetic acid
263 g 95% ethanol
Make to 1 liter

Blocking buffer (50 mM TrisHCl, 5% non-fat dry milk, 0.05% $NaN_3$, pH 7.2)

50 g non-fat dry milk
7.88 g TrisHCl
0.5g $NaN_3$
Make to 800 ml, adjust pH to 7.2, and bring to 1 liter.

Substrate buffer (9.7% diethanolamine, 0.02% $NaN_3$, pH 9.8)

97 ml diethanolamine.

0.2 g NaN$_3$

Make to 800 ml, adjust with HCl to pH 9.8, and bring to 1 liter.

Other Reagents 523 or RS media (described earlier)

Microtiter plates (Immulon 2 'U' well, Dynatech #011-010-3650)

Eppendorf pipettor and tips

Mouse hybridoma culture supernatant or purified monoclonal antibody (IgG producer)

Anti-mouse IgG conjugated to alkaline phosphatase (Sigma #A-5153)

Substrate tablets—p-nitrophenyl phosphate, 5 mg/tablet, (Sigma #104-105)

Procedure

1. Prepare suspensions of strains to be tested in coating buffer from 3-5 day old 523 or RS cultures, adjust OD$_{600}$=0.1 (~10$^8$ cfu/ml).
2. Distribute suspensions in 100 µl aliquots to microtiter wells.
3. Incubate in a circulating air incubator at 37° C. until dry (overnight).
4. Store over dessicant in frost-free refrigerator. (At this point, the plates may be stored for at least 14 weeks).
5. Immediately before use, add 200 µl fixative to each well.
6. Incubate 15 minutes, room temperature.
7. Flick out fixative, blot on paper towel and rinse briefly with distilled water.
8. Flick out water, and wash once for 3 minutes with PBST.
9. Blocking
   A. Block nonspecific binding sites with 200 µl/well of 5% blocking buffer.
   B. Cover plates with parafilm and incubate in moist box for one hour at room temperature.
   C. Wash plates with PBST 3 times by filling wells and leaving after each wash for 3 minutes. Avoid overflowing wells.
10. Monoclonal Antibody
    A. Add purified antibody (1 µg/ml) to wells at 100 µl/well.
    B. Cover plates with parafilm and incubate in moist box at 37° C. in 5% CO$_2$ to maintain pH, incubate for 2.5 hours.
    C. Wash plate as in 9.
11. Blocking
    A. Block nonspecific binding sites with 200 µl/well of 5% blocking buffer heated to 55° C. Do not overheat.
    B. Cover plates with parafilm and incubate in moist box for 20 minutes at room temperature.
    C. Wash plate as in 9.
12. Conjugate
    A. Dilute anti-mouse IgG alkaline phosphatase conjugated IgG in PBST according to tested optimum concentration, usually 1:400. (The method of determining the optimum concentration is conventional in the art.) Add to plate at 100 µl/well.
    B. Cover plates with parafilm and incubate in moist box at 37° C. for 1.5 hours.
    C. Wash plate as in 9.
13. Substrate
    A. Prepare substrate by dissolving p-nitrophenyl phosphate tablets in substrate buffer for a final concentration of 1 mg/ml (1 tablet/5 mls buffer). This must be made up immediately before use. Add to plate at 200 µl/well.
    B. Incubate at room temperature for 30-90 minutes or as long as necessary to observe reaction.
14. Assess results by:
    A. Visual observation.
    B. Measurement on an automated 96-well plate reader at A$_{405\ nm}$ at 30 and 60 minutes.
15. Stop reaction, if desired by adding 50 µl of 3N NaOH to each well and freezing the plate.

NOTE: For identification of many colonies from plates of selective medium RS, 5 day old colonies are picked off the plates with a sterile toothpick and suspended in 100 µl of coating buffer and then proceed as in step 2.

ELISA for detection of Agrobacterium using nitrocellulose solid phase (immunoblot, dot-immunobinding)

Stock solutions 0.5 M Na$_2$HPO$_4$ (dibasic)

3.5 g Na$_2$HPO$_4$ dilute to 500 ml.

0.5 M NaH$_2$PO$_4$ (monobasic)

30.0 g NaH$_2$PO$_4$ dilute to 500 ml.

0.5 M NaPO$_4$, pH 7.2

50 ml monobasic stock, 250 ml dibasic stock, adjust pH by adding more dibasic to raise pH, monobasic to lower.

5×PBS (50 mM NaPO$_4$, 4.5% NaCl)

100 ml 0.5 M NaPO$_4$, pH 7.2 stock
45 g NaCl
Make to 1 liter.

5×PBST (50 mM NaPO$_4$, 4.5 % NaCl, 0.5% Tween)

100 ml 0.5 M NaPO$_4$, pH 7.2 stock
45 g NaCl
5 ml Tween 20 (Sigma)
Make to 1 liter.

5×PBSTM (50 mM NaPO$_4$, 4.5% NaCl, 0.5% Tween, 25% non-fat dry milk).

Add 250 g non-fat dry milk to 800 ml 5X PBST, make to 1 liter with 5X PBST.

1 M Tris base 121.1 g Tris base in 450 ml H$_2$O
Make to 1 liter 0.5 M Na$_2$EDTA 186 g Na$_2$EDTA
800 ml H$_2$O
Adjust to pH 8 by addition of NaOH pellets (~20 g). Dilute to 1 liter.

5 M NaCl

Dissolve 292.2 g NaCl in 800 ml H$_2$O
Bring to 1 liter

NBT (Nitroblue tetrazolium)

75 mg/ml in 70% dimethylformamide (Bethesda Research Labs) (WARNING! DIMETHYLFORMAMIDE is harmful if inhaled, swallowed or absorbed through skin. Avoid breathing vapor. Avoid contact with eyes, skin and clothing. Combustible. Keep away from heat and flame. Wash thoroughly after handling.) Store in freezer.

BCIP (5-bromo-4-chloro-3-indolylphosphate)

50 mg/ml in 70% dimethyl formamide (Bethesda Research Labs) Warning as above. Store in freezer.

Other reagents

Mouse hybridoma culture supernatant (IgG producer)
Anti-mouse-IgG conjugated to alkaline phosphatase (Sigma #A-5153)
Nitrocellulose membranes
523 or RS media (same as described above)
Eppendorf pipettors and tips
Eppendorf tubes and wooden applicator sticks Buffers and working solutions PBS (dilute 5×)

PBST (dilute 5×)

PBSTM (dilute 5×)

Fixative (10% acetic acid, 25% ethanol)

100 ml glacial acetic acid
263 g 95% ethanol
Make to 1 liter

First antibody—monoclonal (0.1 ml per cm$^2$ of membrane)

1 part 5×PBSTM
4 parts H$_2$O
5 parts hybridoma culture supernatant or
1 μg/ml purified antibody in 1×PBSTM Second antibody—conjugate (1:400, 0.1 ml per cm$^2$ of membrane)

10 ml 1×PBSTM
25 μl enzyme conjugated IgG

Substrate buffer (0.1 M Tris-HCl, pH 9.5, 0.1 M NaCl, 50 mM MgCl$_2$; same as Blu-Gene buffer 3)

50 ml 1 M Tris base
10 ml 5 M NaCl
2.38 g MgCl$_2$
make to 400 ml with H$_2$O
Adjust pH with 3 N HCl
Bring to 500 ml.

Substrate (NBT-BCIP: Nitroblue tetrazolium, 0.33 mg/ml, 5-bromo-4-chloro-3-indolyl-phosphate 0.167 mg/ml)

Prepare immediately before use.
Add 33 μl stock NBT to 7.5 ml substrate buffer in petri dish and mix gently: add 25 μl stock BCIP and mix gently.

Stop Buffer (20 mM TrisCl, pH 7.5, 0.5 mM NaEDTA)

20 ml 1 M TrisCl
1 ml 0.5 M NaEDTA
make 900 ml and adjust pH to 7.5 with HCl
Dilute to 1000 ml.

Procedure

1. Grow strains to be tested on 523/RS media for 3-5 days.

2. Make suspension by touching sterile wooden applicator stick to bacterial growth and vortexing in 100 μl sterile dH$_2$O.

3. Label nitrocellulose with #1 pencil, making grid of 1 cm$^2$/strain.

4. Immediately before use, float nitrocellulose on, and then submerge in dH$_2$O for 5 minutes.

5. Air dry by pressing between 2 sheets 3MM filter paper with glass plate and 500 g weight.

6. With membrane still lying on 3MM paper, spot 4 μl (in 2 μl aliquots) of each suspension.

7. Air dry.

8. Immerse in fixative for 15 minutes.

9 Wash with dH$_2$O until water no longer beads up on paper.

10. If papers are to be saved, air dry pressed between 3MM filter papers and store wrapped in foil and dessicated. Can be saved up to 14 weeks.

11. If papers have been saved, wet with distilled water before using.

12. Wash 30 minutes in 100 ml PBSTM (40 rpm on shaker).

13. Incubate 1 hour first antibody, ca. 0.1 ml/cm$^2$ membrane, in sealed container with smallest possible volume (e.g., seal-a-meal bag), RT, 150 rpm on shaker.

14. Wash 3× in 100 mls PBSTM, 3 minutes each, 40 rpm on shaker.

15. Incubate second antibody, ca. 0.1 ml/cm$^2$ membrane, 1 hour, 150 rpm on shaker, RT.

16. Wash 3× in 100 mls PBST, 3 minutes each, 40 rpm on shaker.

17. Incubate in seal-a-meal in dark in substrate (NBT-BCIP) until spots appear (ca. 20 minutes). Longer periods will increase background.

18. Wash in stop buffer to terminate color development.

19. Air dry pressed between 3MM filter papers.

20. Bake 80° C. 5 minutes pressed between dry 3MM filter papers. Store filter paper sandwich wrapped in foil, dessiccated. Photograph through Kodak #5 yellow filter (B&W) and/or in color.

References

1. Ayanaba, A., Weiland, K.D., and Zablotowicz, R.M. 1986. Evaluation of diverse antisera, conjugates, and support media for detecting *Bradyrhizobium japonicum* by indiret enzyme linked immunosorbent assay. *Appl. Environ. Microbiol.* 2:1132-1138.

2. Leach, J.E., Ramundo, B.A., Pearson, D.L., and Claflin, L.E. 1987. Dot-immunobinding assay for detecting *Xanthomonas campestris pv. holicola* in sorghum. *Plant Dis.* 71:30-33.

Modifications

1. Protocol works very well for detecting colonies from 523 medium.

2. When detecting colonies from RS medium, use sterile toothpick to pick up as much growth as possible from each colony and suspend the growth in 50 μl of sterile distilled water.

Proceed with 3.

EXAMPLES

The invention will now be described by reference to specific examples. However, the invention is not to be construed as being limited to the examples.

Unless otherwise specified, all percents, ratios, etc. are by weight.

EXAMPLE 1

Preparation And Characterization of Hybridoma F21-1D3G7C8 and Monoclonal Antibody Produced Therefrom Bacterial strains. *Agrobacterium tumefaciens* biovar 3 strain CG49 was used as the immunogen for production of antibodies. This and other strains used to test the specificity of antibodies are described in Tables 1-3 below. Strains of *Agrobacterium, Pseudomonas*, and *Erwinia* were grown on potato dextrose agar (PDA) (PDA is purchased as a powder from Difco that is mixed with water, autoclaved and poured to solidify in Petri dishes. It contains per liter: Potatoes, infusion from 200 g, Bacto dextrose 20 g and Bacto agar 15 g) or 523 medium (Medium 523 contains per liter of medium: sucrose, 10 g; casein hydrolysate, 8 g; yeast extract, 4 g; $K_2HPO_4$, 3 g; $MgSO_4 \cdot 7H_2O$, 0.3 g; pH adjusted to 7.0; agar, 15 g). (Kado, C.I., Heskett. M.G., and Langley, R.A. 1972. Studies on *Agrobacterium tumefaciens*: characterization of strains 1D135 and B6, and analysis of the bacterial chromosome, transfer RNA and ribosomes for tumor inducing ability. Physiol. Plant Pathol. 2:47-57). Rhizobium strains were grown on yeast mannitol agar (per liter: 1 g yeast extract, 10 g mannitol, 0.65 g $K_2HPO_4 \cdot 3H_2O$, 0.2 g $MgSO_4 \cdot 7H_2O$, 0.1 g NaCl, 15 g agar, pH 7.4). Cultures were grown at 28° C.

TABLE 1

Agrobacterium strains used for testing specificity of monoclonal antibody AbF21-1D3G7C8.

| Strain | Isolated from | Received from | Geographic origin | Previously designated | Tumorigenicity | Biovar |
|---|---|---|---|---|---|---|
| CG49 | Vitis gall | a | NY | — | + | 3 |
| CG60 | Vitis gall | a | NY | — | + | 3 |
| CG90 | Vitis gall | a | NY | — | + | 3 |
| CG98 | Vitis gall | a | VA | — | + | 3 |
| CG102 | Vitis gall | a | VA | — | + | 3 |
| CG230 | Vitis sap | a | NY | — | + | 3 |
| CG472 | Vitis roots | a | WA | — | + | 3 |
| CG474 | Vitis roots | a | NM | — | + | 3 |
| CG481 | Vitis roots | a | NY | — | — | 3 |
| CG482 | Vitis roots | a | WA | — | — | 3 |
| CG483 | Vitis roots | a | WA | — | — | 3 |
| CG485 | Vitis roots | a | NY | — | + | 3 |
| CG486 | Vitis roots | a | NY | — | ± | 3 |
| CG624 | Vitis callus | a | NY | — | + | 3 |
| CG626 | Vitis callus | a | NY | — | + | 3 |
| CG673 | Vitis sap | a | CA | — | — | 3 |
| CG953 | Vitis gall | C. Panagopoulos | Crete | Ag 57-81 | + | 3[b] |
| AA34 | Vitis gall | G. Ercolani | Afganistan | — | + | 3 |
| IPV-B02152 | Vitis gall | C. Bazzi | Italy | — | + | 3 |
| NW-161 | Vitis gall | E. Biehn | W. Germany | NW-161 | + | 3 |
| CG965 | Vitis gall | M. Lopez | Spain | 550-2 | + | 3 |
| CG967 | Vitis gall | M. Lopez | Spain | 339-6 | + | 3 |
| IPV-B02147 | Vitis callus | C. Bazzi | Italy | — | + | 3 |
| CG969 | Vitis gall | C. Bazzi | Italy | IPV-B02156b | + | 3 |
| CG971 | Vitis callus | C. Bazzi | Italy | IPV-B02111 (7) | + | 3 |
| CG976 | Vitis gall | M. Lopez | Spain | 565-5 | + | 3 |
| CG90 | Vitis gall | a | NY | — | — | 1 |
| CG210 | Vitis sap | a | NY | — | — | 1 |
| CG219 | Vitis sap | a | NY | — | ± | 1 |
| CG401 | soil | a | NY | — | + | 1 |
| CG429 | soil | a | VA | — | — | 1 |
| CG462 | soil | a | NM | — | — | 1 |
| CG628 | Vitis callus | a | NY | — | + | 1 |
| CG656 | Vitis callus | a | NY | — | + | 1 |
| CG674 | Vitis sap | a | CA | — | — | 1 |
| CG920 | Clematis gall | a | NY | — | + | 1 |
| R-6 | Rosa gall | R. S. Dickey | NY | — | + | 1 |
| CG939 | Chrysanthemum | a | NY | — | + | 1 |
| B6 | c | R. S. Dickey | IA | — | + | 1 |
| Ag125 | Vitis gall | C. Panagopoulos | Greece | — | — | 1 |
| CG962 | Aster gall | a | CT | — | + | 1 |
| CG972 | Vitis gall | M. Lopez | Spain | 360-1 | — | 1 |
| NW-310 | Vitis gall | E. Biehn | W. Germany | — | — | 1 |
| CG974 | Vitis gall | C. Bazzi | Italy | IPV-B2150bA | — | 1 |
| C58 | Prunus gall | R. S. Dickey | NY | — | — | 1 |
| CG414 | soil | a | NY | — | + | 2 |
| CG423 | soil | a | NY | — | — | 2 |
| CG438 | Vitis roots | a | WA | — | — | 2 |
| A-4 | Rosa gall | L. Moore | CA | — | +[d] | 2 |
| K-47 | c | L. Moore | c | — | +[d] | 2 |
| R-10 | Rosa gall | R. S. Dickey | AZ | — | + | 2 |
| SRA-1 | Rosa gall | R. S. Dickey | PA | — | + | 2 |

[a] Isolated in inventors' laboratory.
[b] Limited-host-range (Panagopoulos. C. G., and Psallidas. P. G. 1973. Characteristics of Greek isolates of *Agrobacterium tumefaciens* (E. F. Smith & Townsend) Conn. J. Appl. Bacteriol. 36:233-240. All others are wide-host-range (Burr. T. J., and Katz. B. H. 1984. Grapevine cutting as potential sites of survival and means of dissemination of *Agrobacterium tumefaciens*. Plant Dis. 68:976-978 and Sule, S.. 1978. Biotypes of *Agrobacterium tumefaciens* in Hungary. J. Appl. Bacteriol. 44:207-213.
[c] Unknown
[d] Rhizogenic teratoma

TABLE 2

Other bacterial species used for testing specificity of monoclonal antibodies.

| Strain | Species | Received from |
|---|---|---|
| USDA 110 | Rhizobium meliloti | T. LaRue |
| 128C53 | R. leguminosarum | T. LaRue |
| 1021 | Bradyrhizobium japonicum | T. LaRue |
| EA266 | Erwinia amylovora | S. Beer |
| EA273 | E. amylovora | S. Beer |
| TL-3 | Pseudomonas fluorescens/putida | a |
| BK-1 | P. fluorescens/putida | a |

[a]Isolated in inventors' laboratory.

TABLE 3

Unidentified saprophytes associated with *Vitis vinifers* L. used for testing specificity of monoclonal antibody.

| Source | Condition of vines | Geographic origin | Number of strains tested |
|---|---|---|---|
| Sap | galled | NY | 7 |
| Sap | healthy[a] | NY | 7 |
| Sap | healthy[b] | NY | 12 |
| Sap from roots | galled | WA | 2 |
| Rhizosphere | galled | WA | 15 |

[a]Pinot Chardonnay free of Agrobacterium planted in apple orchard site.
[b]Pinot Chardonnay free of Agrobacterium planted in recently cleared vineyard site.

Immunogen preparation. Three-day-old PDA cultures of CG49 were harvested by washing plates with calcium-magnesium-free phosphate buffered saline (PBS-CMF: 1.5 mM $KH_2PO_4$, 8.1 mM $Na_2PO_4$, 2.7 mM KCl, 150 mM NaCl, pH 7.4), washed by 3 cycles of centrifugation (10000×g, 10 min) and resuspension in PBS-CMF. Suspensions were adjusted to $A_{600nm}=0.1$ with PBS-CMF and heated (10 min, 80° C.) prior to immunization.

Monoclonal antibody production. BALB/c mice (Jackson Laboratories, Bar Harbor, ME) were immunized at 6 weeks of age (300 µl intraperitoneal and 200 µl subcutaneous) with bacterial suspensions mixed 1:1 with Freund's complete adjuvant (Freund, J. and McDermott, K. 1942. Sensitization to horse serum by means of adjuvants. *Proc. Soc. Exp. Bio. NY* 49:548) Booster injections (500 µl intraperitoneal) 2 weeks after immunization were prepared with Freund's incomplete adjuvant (Freund. J. and McDermott. K. 1942. Sensitization to horse serum by means of adjuvants. *Proc. Soc. Exp. Bio. NY* 49:548). Three days prior to fusion 250 µl intraperitoneal booster injections were administered. Mouse spleens were surgically removed 5 weeks after initial immunization and splenocytes prepared for fusion using conventional methods as described in "Monoclonal Hybridoma Antibodies" Techniques and Applications. Hurrell, John G.R. Editor, CRC Press, Inc., Boca Raton, FL (1982), 231 pp. and "Monoclonal Antibodies" Principles and Practice. Second Edition. Goding, James W. Academic Press. (1986) 293 pp. $10^8$ splenocytes were fused with $10^7$ SP2/O-AG14 myeloma cells (American Type Culture Collection, Rockville, MD) in 1 ml 50% polyethylene glycol (MW 1450) and diluted to 15 ml with Dulbecco's modified Eagle medium, 0.45 % glucose amended with 1.5 mM HEPES, 44 mM $NaHCO_3$, 0.1 mM nonessential amino acids, 2 mM L-glutamine, 0.45 mM sodium pyruvate, $10^5$ units/liter penicillin G, and $10^5$ units/liter streptomycin (DMEM). Cells were centrifuged, resuspended in 10 ml DMEM amended with 20% fetal bovine serum (FBS), $1.02 \times 10^{-4}$ M hypoxanthine, $4 \times 10^{-7}$ M aminopterin, and $1.65 \times 10^{-4}$ mM thymidine (DMEM/HAT/20%FBS), diluted to 70 ml with DMEM/HAT/20%FBS, and distributed in 100 µl aliquots to seven 96 well cell culture plates. Culture plates were seeded the previous day with mouse macrophages to provide feeder cells ($10^3$/well in 100 µl DMEM/HAT/20%FBS). Mouse macrophages were collected by peritoneal lavage of pristane-primed mice. Cell cultures were fed by aspiration of spent medium and replacement with DMEM/HAT/20%FBS 4-6 days after fusion, DMEM/HAT/20%FBS (lacking aminopterin) 6-11 days after fusion, and screened for antibody production 11-13 days after fusion. Hybrids secreting antibodies which reacted with *Agrobacterium tumefaciens* biovar 3 were cloned and subcloned by limiting dilution. Selected cell cultures were scaled up to 500 ml in DMEM/20%FBS from which supernatants were harvested after 7-10 days by centrifugation. Cloned cell line F21-1D3G7C8, a hybridoma according to the present invention, was used to produce ascites fluid by intraperitoneal injection of two 11 week old pristane-primed BALB/c mice with $2 \times 10^6$ hybridoma cells in 500 µl PBS-CMF ("Monoclonal Hybridoma Antibodies" Techniques and Applications. Hurrell, John G.R. Editor, CRC Press, Inc., Boca Raton, FL (1982) 231 pp). Cell culture supernatants and ascites fluids were stored frozen or at 4° C. after addition of $NaN_3$ (0.05%).

Screening of hybridomas. Hybridoma culture supernatants were tested initially for production of antibodies specific to *Agrobacterium tumefaciens* biovar 3 in a microtiter plate enzyme-linked immunosorbent assay (microELISA). Antigens were prepared by washing bacterial cells harvested from 3-day-old PDA or 523 cultures. Bacteria were suspended in phosphate-buffered saline (PBS, 0.01 M sodium phosphate. 0.85% NaCl, pH 7.2)+0.05% sodium lauryl sarcosine, centrifuged (10.000×g, 10 min), and then suspended and pelleted twice more in PBS. Prior to final centrifugation suspensions were heated for 10 minutes at 80° C. The final pellet was suspended in coating buffer (40 mM sodium carbonate, pH 9.6) and adjusted to $A_{600nm}=0.1$.

All incubations were in moist chambers and at 37° C. unless otherwise noted. Microtiter plates (Immulon 2 "U" well, Dynatech) were incubated overnight with 100 µl of antigen/well. Antigen was flicked out and wells were washed 3 times, for 3 minutes each, with PBS+0.05% Tween20 (PBST), and then plates were incubated at room temperature for 1 hour with 200 µl blocking buffer (5% nonfat-dry milk in 50 mM TRIS-HCl, pH 7.2) per well. Following washing (as above), hybridoma culture supernatant (100 µl/well) was added for 2.5 hour incubation in a moist chamber at 37° C., 5% $CO_2$. Plates were washed (as above) and incubated 20 minutes at room temperature with 200 µl/well blocking buffer which had been heated at 55° C. After another round of washing, plates were incubated 1.5 hour with 100 µl/well goat-anti-mouse IgG-alkaline phosphatase conjugate (Sigma), diluted 1:1000 or 1:400 in PBST. Plates were washed a final time, as before, and 200 µl substrate (1 mg/ml p-nitrophenylphosphate in 9.7% diethanolamine, pH 9.8), was added to each well and incubated at room temperature. $A_{405nm}$ was measured periodically on a Dynatech MR580 MICROELISA auto reader.

Isotype determination. Isotypes were determined in Ouchterlony double diffusion tests using anti-mouse immunoglobulins (Sigma) in 0.8% noble agar buffered with 1.5 mM borate, pH 8.3, 5 mM KCl, 0.85% NaCl ("Monoclonal Hybridoma Antibodies" Techniques and Applications. Hurrell, John G.R. Editor, CRC Press, Inc., Boca Raton, FL (1982) 231 pp. and "Monoclonal Antibodies: Principles and Practice. Second Edition. Goding, James W. Academic Press. (1986) 293 pp.)

The isotype of monoclonal antibody AbF21-1D3G7C8, the monoclonal antibody secreted by hybridoma line F21-1D3G7C8, was determined to be IgG1.

Purification of antibody. Antibody AbF21-1D3G7C8 was purified from ascites fluid and culture supernatant using protein A affinity chromatography (AFFI-GEL MAPS II kit, Bio-Rad), according to the manufacturers instructions, except that culture supernatants were not concentrated prior to chromatography.

Specifically, 50 ml of culture supernatant was mixed with 50 ml of Bio-Rad binding buffer and applied to a 5 ml bed volume of affi-gel protein A in a $1 \times 10$ cm column. The column was washed with 50 ml of Bio-Rad binding buffer and IgG was elected with 20 ml of Bio-Rad elution buffer, or until the absorbance of the eluate at 280 nm approached 0. The fractions of IgG were combined and neutralized with 32 $\mu$l/ml of 1 M TrisHCl, pH 9.0.

The concentration of antibody was estimated by UV spectrophotometry following purification. Binding buffer fractions were dialyzed against PBS and tested in a microELISA to determine efficiency of binding of antibody to the protein A column.

Large volume cultures of F21-1D3G7C8 yielded about 80 $\mu$g/ml IgG1. Following purification and concentration on the protein-A column, concentration of IgG1 was 295 $\mu$g/ml. Less than 1.0% of antibody activity passed through the column with the binding buffer. Ascites A24 and A25 yielded 1.7 mg/ml (3 ml) and 750 $\mu$g/ml (3.5 ml), respectively. Saturation with AbF21-1D3G7C8 was reached at about 1 $\mu$g/ml in microELISA tests using CG49 as antigen.

Specificity of antibody. The microELISA was modified for testing of large numbers of strains by drying antigens suspended in coating buffer in a 37° C. circulating air incubator, rather than coating overnight in a moist chamber. Immediately prior to use, dried plates were incubated with 200 $\mu$l/well fixative (25% ethanol, 10% acetic acid) for 15 minutes, room temperature, and then rinsed with distilled water, after which the previously described microELISA protocol was followed except that 5% $CO_2$ was omitted in incubation with monoclonal antibody. Purified antibody (1 $\mu$g/ml) was used in specificity tests. The strains tested are described in Tables 1-3 above.

All 26 strains of *Agrobacterium tumefaciens* biovar 3 tested reacted with AbF21-1D3G7C8; no other strains (19 strains of Agrobacterium biovar 1, 7 strains of Agrobacterium biovar 2, 7 strains from other genera, and 43 strains of unidentified saprophytes associated with grapevines in the field. Tables 1-3) reacted with this antibody. Specificity of AbF21-1D3G7C8 for *Agrobacterium tumefaciens* biovar 3 was not affected by tumorigenicity of the strains tested.

Positive reaction of AbF21-1D3G7C8 with all *Agrobacterium tumefaciens* biovar 3 strains tested from North America, Europe, and Asia, and the absence of cross-reaction with other biovars of Agrobacterium, other species of plant pathogens, and saprophytes associated with vines, represents a significant improvement over previous attempts to produce biovar specific antisera for diagnosis of Agrobacterium (Keane, P.J., Kerr, A., and New, P.B. 1970. Crown gall of stone fruit. II. Identification and nomenclature of Agrobacterium isolates. Aust. J. Biol. Sci. 23:485-595 and Miller, H.J., and Vruggink, H. 1981. An assessment of biochemical and serological tests for *Agrobacterium radiobacter* subsp. *tumefaciens*. Phytopath. Z. 102:292-300). Most *Agrobacterium tumefaciens* biovar 3 strains tested were typical wide-host-range strains (Burr, T.J., and Katz, B.H. 1984. Grapevine cuttings as potential sites of survival and means of dissemination of *Agrobacterium tumefaciens*. Plant Dis. 68:976-978 and Sule, S., 1978. Biotypes of Agrobacterium tumefaciens in Hungary. J. Appl. Bacteriol. 44:207-213), but the limited-host-range strains (Panagopoulos, C.G., and Psallidas, P.G. 1973. Characteristics of Greek isolates of *Agrobacterium tumefaciens* (E.F. Smith & Townsend) Conn. J. Appl. Bacteriol. 36:233-240) tested reacted as expected, indicating that the host range variation is independent of reaction with AbF21-1D3G7C8.

Drying and fixation of antigens on microtiter plates significantly improved microELISA tests. $A_{405nm}$ readings of tests of dried, fixed plates coated with CG49 were 5-10 times higher than moist coated plates under the same assay conditions, while readings of negative controls did not increase significantly. Also, dried plates could be stored dessicated at 4° C. for at least 3 months (the longest period tested) without detectable loss of antigenic activity.

Sensitivity of modified microELISA. A sterile distilled water (SDW) suspension of washed *Agrobacterium tumefaciens* biovar 3 CG49 cells was diluted serially in SDW and coating buffer. Aliquots of SDW dilutions were spread on PDA and colonies were counted after 5 days. 100 $\mu$l aliquots of coating buffer suspensions were used for the modified microELISA, described above, to determine the number of viable *Agrobacterium tumefaciens* biovar 3 required to give positive results.

AbF21-1D3G7C8 detected as few as $2.3 \times 10^4$ cells/well in modified microELISA ($A_{405nm} = 0.332$ at 40 min, vs. 0.011 for control, using antibody concentration of 1 $\mu$g/ml and conjugate dilution of 1:400, $P < 0.001$). Fewer cells gave $A_{405nm}$ readings which were not significantly different from negative controls.

EXAMPLE 2

Indexing Grapevine Propagation Material For The Presence Of Agrobacterium Tumefaciens Biovar 3

Isolation of bacterium from dormant cuttings

Bacteria were isolated from dormant cuttings by either of 2 methods.

Method 1: This method is a modification of the method described by Lehoczky (*Vitis* 10:215-221 (1971) and Burr and Katz (*Plant Disease* 68 No.11:976-978 (1984)). Cuttings that had three buds were taken from a grapevine. The cuttings were surface sterilized in a 0.53% NaOCl solution for 3 minutes, rinsed in tap water and 1 cm was cut from each end to remove any residual NaOCl. The sterilized cuttings were potted in a sterile potting mixture comprising moist perlite placed in a greenhouse and maintained at 22-24° C. until callus was initiated at the base of the cutting.

Tissue pieces (about 3 to 4 mm diameter) were then excised from different places of the callus with a sterile scalpel and the surfaces quickly sterilized with 70% ethyl alcohol. The pieces were then washed in sterile distilled water and were macerated in 0.5 ml sterile water in a watch glass. The tissue pieces were separated from the liquid and the liquid diluted 10- and 100-fold with sterile water. 0.15 ml of the diluted liquid was then smeared with a glass rod onto the surface of selective medium RS (0.20 g/L $MgSO_4$; 0.90 g/L $K_2HPO_4$; 0.70 g/L $KH_2PO_4$; 4.0 g/L adonitol; 0.14 g/L yeast extract; 0.20 g/L NaCl: 1.0 g/L boric acid; and 15.0 g/L agar: pH 7.2. The mixture was auto-claved and cooled to 50° C. and the following were added by filter sterilization: 0.08 g/L triphenyl tetrazolium chloride; 0.02 g/L D-cycloserine, 0.02 g/L trimethoprim: and 0.25 g/L cycloheximide.) in 10 cm diameter Petri-dishes. The cultures were incubated for 4-5 days at 28° C. in a thermostat, and 5 colonies (designated samples 1 to 5) were isolated for identification as *Agrobacterium tumefaciens* biovar 3.

Method 2: This method is described in Bazzi et al, *Bulletin OEPP/EPPO Bulletin* 17:105-112 (1987). Cuttings (20 cm long, 6-12 mm in diameter, with 1 to 3 nodes) were washed under running tap water and blotted dry. The proximal end of each cutting was fitted with a piece of Tygon tubing that was attached to a piece of glass tubing. The glass tubing was inserted through a stopper of a side-arm vacuum flask and into a centrifuge tube contained within the flask. The distal end of the cutting was fitted with Tygon tubing that was attached to a buret containing washing fluid (sterile distilled water). Washing fluid was forced through the cuttings by vacuum pressure obtained using a high-vacuum pump. Aliquots (0.1 ml) of washing fluid were smeared on RS medium (described above) and the cultures were incubated for 4-5 days at 28° C. in a thermostat. 5 colonies (designated samples 1 to 5) were isolated for identification as *Agrobacterium tumefaciens* biovar 3.

Samples obtained by methods 1 and 2 above are then analyzed by microELISA or immunoblot as follows.

Samples for analysis by microELISA: Each of the five colonies designated samples 1-5 for identification as *Agrobacterium tumefaciens* biovar 3 is collected with a toothpick, and suspended in 100 μl coating buffer, and then diluted with coating buffer (40 mM $NaCO_3$, pH 9.6, 0.05 % $NaN_3$) until slightly turbid to the eye, or of $OD_{600nm}=0.1$ as determined by spectrophotometer. A stain of *Aorobacterium tumefaciens* biovar 3 (e.g. CG49, ATCC 53691) is also grown on RS medium and treated in the same manner for use as a positive control. Strains of *Agrobacterium tumefaciens* biovars 1 and 2 (e.g. strains C58 (biovar 1) and K84 (biovar 2) are also grown on RS medium and treated in the same manner for use as negative controls. 100 μl aliquots of each of these suspensions are then placed in the wells of three or more microtiter plates. Three or more wells are also filled with coating buffer (no bacteria present) to serve as additional negative controls. Plates are placed in a 37° C. circulating air incubator to dry overnight.

A modified microELISA is performed as described above. Where one or more samples from a given cutting gives a reaction signficantly stronger than the negative controls (*Agrobacterium tumefaciens* biovar 1 and 2) (as determined by visual inspection, or by comparison of $A_{405nm}$ spectrophotometer readings using a Student's T-test), and where the biovar 1 and 2 controls are not significantly different from the coating buffer only control, the cutting is determined to be infected with *Agrobacterium tumefaciens* biovar 3. If the reactions of biovar 1 and 2 controls are stronger than the coating buffer control, or if the reaction of the biovar 3 control is not significantly stronger than the biovar 1 and 2 controls, the test is invalid, and must be repeated.

Samples for analysis by immunoblot: Each of the five colonies designated samples 1-5 for identification as *Agrobacterium tumefaciens* biovar 3 is collected with a toothpick, and suspended in 100 μl distilled water. A strain of *Agrobacterium tumefaciens* biovar 3 (e.g. CG49, ATCC 53691) is also grown on RS medium and treated in the same manner for use as a positive control. Strains of *Agrobacterium tumefaciens* biovars 1 and 2 (e.g. strains C58 (Biovar 1) an K84 (Biovar 2)) are also grown on RS medium and treated in the same manner for use as negative controls. 4 μl aliquots of each of these suspensions are then spotted on duplicate moist nitrocellulose membranes (membranes A and B), air dried, and fixed as described above for ELISA using nitrocellulose membranes as solid support (immunoblot).

The immunoblot procedure is performed as described above on one of the membranes (membrane A). The other membrane is subjected to a modification of the immunoblot procedure in which unamended PBST is substituted for 1 μg/ml AbF21-1D3G7C8. This membrane serves as a control for non-specific binding of the anti-mouse IgG alkaline phosphatase conjugated IgG to bacterial cells. Where one or more samples from a given cutting on membrane A gives a reaction significantly stronger than the negative controls (*Agrobacterium tumefaciens* biovar 1 and 2) on membrane A than the sample itself on membrane B (as determined by visual inspection). the cutting is determined to be infected with *Agrobacterium tumefaciens* biovar 3. If biovar 1 and 2 controls react more strongly on membrane A than membrane B, or if biovar 3 on membrane A does not react more strongly than biovar 3 on membrane B, or if biovar 3 on membrane A does not react more strongly than biovars 1 and 2 on membrane A, the test is invalid, and must be repeated.

EXAMPLE 3

Direct Diagnosis of Agrobacterium Tumefaciens Biovar 3 Associated Grapevine

Diagnosis from Crown Gall Tissue

A sample of gall tissue (0.2-1.0 g) is ground in distilled water (5 ml/g tissue) in a mortar and pestle. A portion of wood from an uninfected plant of the same cultivar is treated in a similar manner to serve as a negative control.

Three serial ten-fold dilutions of each preparation are made using the coating buffer described in Example 1. Next, at least three replicates of 100 μl each of dilutions of the sample to be diagnosed and control preparations are placed in wells of microtiter ELISA plates and dried overnight in a circulating air incubator at 37° C.

A modified microELISA as described in Example 1 is performed on each well. Where mean ELISA readings from gall samples are significantly different as determined by Student's t-Test (*Statistical Methods,* 6th edition, George W. Snedecor and Wm. G. Cochran, Iowa State University Press, Ames, Iowa, 593 pp) from control preparations at the same dilution, the sample is positive.

Alternatively, a sample of gall tissue and a portion of wood from uninfected plants are separately ground as described above in a mortar and pestle and three serial ten-fold dilutions of each preparation are made with distilled water.

Next, three replicates of 4 μl each of dilutions of the sample and control preparations are applied to duplicate moist nitrocellulose membranes (membranes A and B), air dried, and fixed as described for ELISA using nitrocellulose membranes as solid support (immunoblot).

The immunoblot procedure is performed as described above on one of the membranes (membrane A). The other membrane is subjected to a modification of the immunoblot procedure in which unamended PBST is substituted for 1 μg/ml AbF21-1D3G7C8. This membrane serves as a control for non-specific binding of the anti-mouse IgG alkaline phosphatase conjugated IgG to bacterial cells. Where spots from a given sample on membrane A give a reaction significantly stronger than the negative controls (uninfected wood on membrane A, and the sample itself on membrane B) (as determined by visual inspection), the gall is determined to be infected with *Agrobacterium tumefaciens* biovar 3. If uninfected wood controls react more strongly on membrane A than on membrane B, the test is invalid, and must be repeated.

Diagnosis from Non-Systomatic Grape Cuttings

Cuttings are flushed as described in Example 2 (Method 2) but using coating buffer (as described in Example 1) as the flushing fluid. Cuttings known to be uninfected are used as a negative control and treated in the same manner.

Each preparation is then diluted ten-fold in coating buffer. Three replicates of 100 μl each of dilutions of the sample and control preparations are placed in wells of microtiter ELISA plates and dried overnight in a circulating air incubator at 37° C.

A modified microELISA is performed as described above and the results analyzed as described above in this Example.

Alternatively, cuttings (to be diagnosed and as negative control) are flushed as described above only using distilled water as flushing fluid.

Ten-fold dilutions of each preparation are made in distilled water, and three replicates of 4 μl each of dilutions of the sample and control preparations are spotted on nitrocellulose membranes.

ELISAs for nitrocellulose as a solid support are performed as described above for the direct diagnosis method using crown gall tissue, and the results are analyzed also as described above for the direct diagnosis method using crown gall tissue.

While the invention has been described in detail and with reference to specific embodiments thereof, it will be apparent to one skilled in the art that various changes and modifications can be made therein without departing from the spirit and scope thereof.

What is claimed is:

1. A monoclonal antibody which has all of the identifying characteristics of the monoclonal antibody secreted by murine hybridoma cell line F21-1D3G7C8 having ATCC deposit no. HB 9463.

2. A hybridoma which has all of the identifying characteristics of murine hybridoma cell line F21-1D3G7C8 having ATCC deposit no. HB 9463.

* * * * *